US006651485B2

(12) United States Patent
Hubrich et al.

(10) Patent No.: US 6,651,485 B2
(45) Date of Patent: Nov. 25, 2003

(54) METHOD FOR DETERMINING THE VISCOSITY OF AN OPERATING LIQUID OF AN INTERNAL COMBUSTION ENGINE

(75) Inventors: Stefan Hubrich, Filderstadt (DE); Michael Pulvermueller, Deggingen (DE)

(73) Assignee: Conti Temic microelectronic GmbH, Nuremberg (DE)

( * ) Notice: Subject to any disclaimer, the term of this patent is extended or adjusted under 35 U.S.C. 154(b) by 0 days.

(21) Appl. No.: 10/146,764

(22) Filed: May 15, 2002

(65) Prior Publication Data

US 2002/0174710 A1 Nov. 28, 2002

(30) Foreign Application Priority Data

May 22, 2001 (DE) .......................................... 101 24 890

(51) Int. Cl.$^7$ .............................................. G01M 15/00
(52) U.S. Cl. ...................................... 73/35.02; 73/35.02
(58) Field of Search .......................... 123/179.17, 381, 123/446, 447, 481, 491, 497, 501, 196 R, 456, 467; 73/35.02, 54.01, 54.07, 54.08

(56) References Cited

U.S. PATENT DOCUMENTS

| 4,694,793 A | | 9/1987 | Kawakita et al. |
| 5,176,115 A | * | 1/1993 | Campion ................ 123/179.17 |
| 5,181,494 A | * | 1/1993 | Ausman et al. ............. 123/446 |
| 5,568,842 A | | 10/1996 | Otani |

FOREIGN PATENT DOCUMENTS

| DE | 3638714 | 9/1990 |
| DE | 4131969 | 4/1993 |
| DE | 19518776 | 11/1996 |
| DE | 19636422 | 12/1998 |
| DE | 19747737 | 5/1999 |
| DE | 19837552 | 10/1999 |

\* cited by examiner

Primary Examiner—Kamand Cuneo
Assistant Examiner—Monica D. Harrison
(74) Attorney, Agent, or Firm—W. F. Fasse; W. G. Fasse

(57) ABSTRACT

A method of determining the viscosity of an operating liquid, such as engine oil, in an internal combustion engine uses a sensor having a measuring chamber for determining the liquid level and its variation. The measuring chamber is connected via a damping device to a reservoir of the operating liquid. On starting the internal combustion engine, the variation in the liquid level is measured in the measuring chamber of the sensor and the variation of the level over time is used as a measure for determining the viscosity.

16 Claims, 1 Drawing Sheet

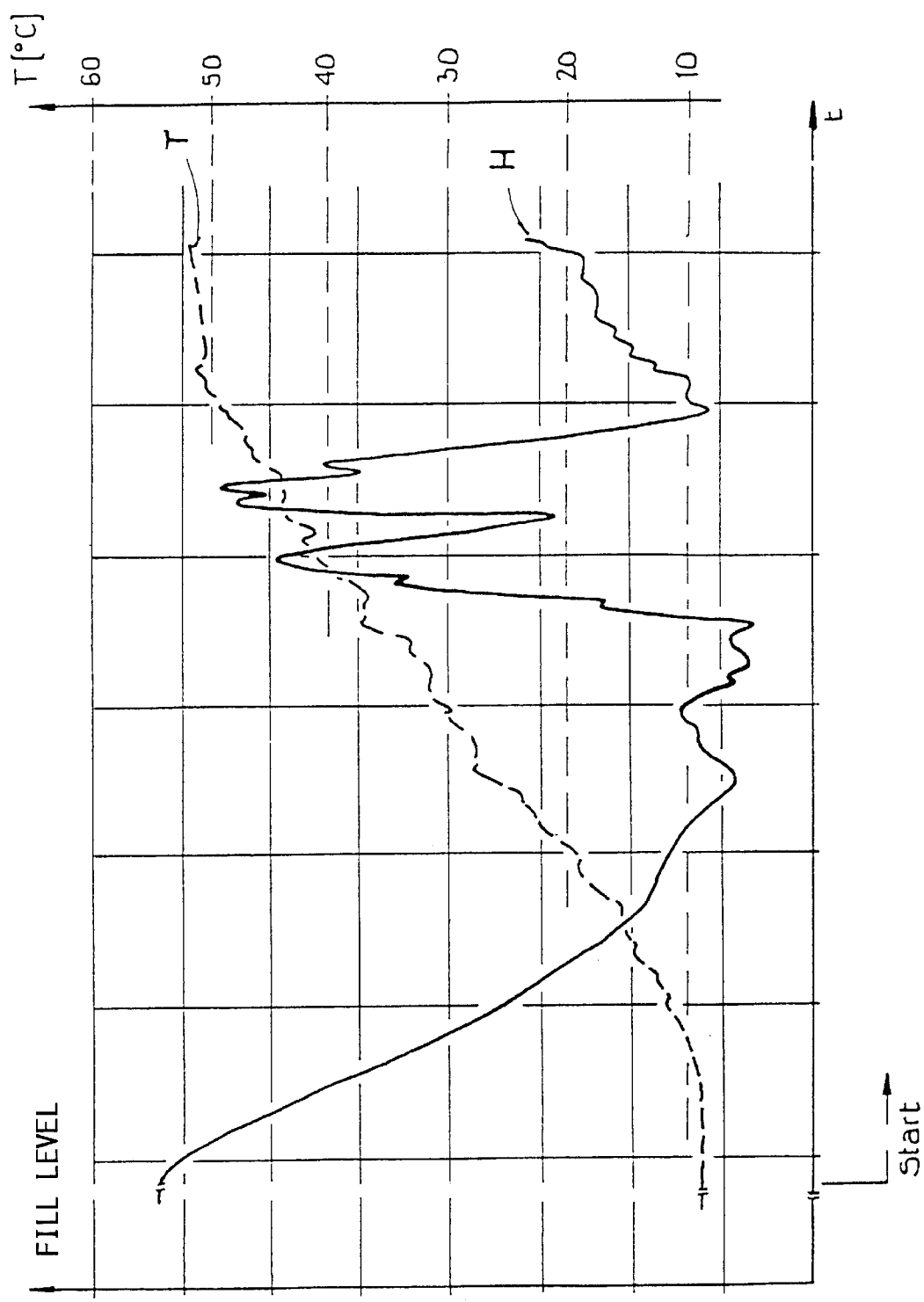

METHOD FOR DETERMINING THE VISCOSITY OF AN OPERATING LIQUID OF AN INTERNAL COMBUSTION ENGINE

FIELD OF THE INVENTION

The invention relates to a method for determining the viscosity of an operating liquid, such as the engine oil, of an internal combustion engine.

BACKGROUND OF THE INVENTION

A method of this kind is known from DE 195 18 776 A1 which describes a method for establishing the viscosity of an operating liquid on the basis of the changes in the level of the operating liquid over a period of time. In this known method, the viscosity of the engine oil is determined after having turned off an internal combustion engine by measuring the variation of the engine oil level over a period of time. The return of the engine oil to the sump after the engine has been turned off takes place with a time delay that depends on the viscosity. Apart from the variation of the level of the oil against time, the oil temperature is also a factor in the known method because the viscosity of the engine oil generally depends on its temperature.

Apart from these variables that are to be measured in a simple manner, the measurement of the viscosity in accordance with the known method is, however, also influenced by other variables. For instance, a high dynamic loading of the internal combustion engine over a period of time immediately before it is turned off can lead to foaming of the engine oil. The consequent slower change in level after turning the engine off results in corruption of the actual measurement. An objective measured variable for the dynamic loading of the internal combustion engine cannot, however, be determined in a simple manner.

Furthermore, when the internal combustion engine is turned off while the vehicle is in an inclined position, this also has an adverse effect on the return flow of the engine oil into the sump.

Another disadvantage is due to the fact that the electronic modules needed for the measurement still have to be actively operated for the required period of time after the internal combustion engine has been turned off.

SUMMARY OF THE INVENTION

The object of the invention is to specify a method for determining the viscosity of an operating liquid of an internal combustion engine, whereby the method supplies a precise result with few measured variables and is performed while the internal combustion engine is in operation.

This object is achieved by a method according to the invention, having the following features.

In the method for determining the viscosity of an operating liquid of an internal combustion engine of a vehicle by determining the level of the operating liquid, a sensor is provided for establishing the level of the operating liquid, said sensor having a measuring chamber that is connected via a damping device to a reservoir of the operating liquid. During the starting operation of the internal combustion engine, the variation of the level (H) of the operating liquid in the measuring chamber of the sensor is measured. The viscosity is determined from the variation of the level (H) against time. As opposed to the methods known from DE 195 18 776 A1, a sensor is used here that has a structure which damps the measured value curve. Acquisition of the measured values at the time of starting the internal combustion engine has the decisive advantage that controlled marginal conditions regularly prevail.

In a first embodiment of the method, the temperature (T) of the operating liquid is measured during the starting operation and is accounted for in the determination of the viscosity. This allows the values obtained for the viscosity to be corrected at the start to allow for the influence of temperature.

In a second embodiment of the method, the rotational speed of the internal combustion engine is also measured after the starting operation and allowed for when determining the viscosity. This allows the values obtained for the viscosity to be corrected at the start to allow for the influence of the change in operating liquid volume resulting from the rotational speed.

In a further embodiment of the method, the temperature of the operating liquid during the starting operation and the variation of the temperature of the operating liquid against time are also taken into account when determining the viscosity.

The invention will now be described with reference to an example embodiment and the single accompanying drawing FIGURE.

BRIEF DESCRIPTION OF THE DRAWING

The single drawing FIGURE graphically shows the measured variation of the level and the variation of the temperature of the engine oil versus time after a cold start.

DETAILED DESCRIPTION OF THE INVENTION

In the following embodiment example, the method for determining the viscosity will be explained on the basis of the engine oil in an internal combustion engine. With an oil level sensor having a mechanical structure that damps the fluctuations of the level in its measuring chamber, the level in the measuring chamber of the sensor follows the level in the reservoir with a time delay. If there is a difference between the two levels, the damping causes the liquid to flow only slowly out of or into the measuring chamber. The time taken for compensation depends on the viscosity of the oil.

During the start phase of an internal combustion engine, the engine oil in the reservoir of the oil sump reduces because of the oil taken up by the running engine. This means that the mean value of the oil level in the reservoir of the oil sump reduces after starting the engine by the amount that is now to be found in the oil circuit. This change in the reservoir volume takes place at high speed and, in a first approximation, by a constant amount.

The oil level in the measuring chamber of the oil level sensor follows, especially when the oil is cold because of the higher viscosity due to the temperature, the change in level in the reservoir with a time constant that is adequate for one measurement. The damping mechanical structure ensures that the oil level in the measuring chamber of the sensor slowly approaches the level in the reservoir. Under these operating conditions, the oil level sensor acts like an outlet viscometer. This circumstance is utilized by the present method in order to determine the viscosity of the oil from the drop in measured level H against time. Immediately after engine start, the change in the oil level after a period of time is a measure of the viscosity of the engine oil. The gradient $-dH/dt > 0$ is proportional to the viscosity of the oil.

The FIGURE shows a diagram in which the curve of the measured oil level H and the temperature curve of the engine oil against time can be seen after a cold start. After the engine has started, the measured level H of the engine oil drops with an essentially constant gradient over a first period of time. Only later, when the temperature of the oil is correspondingly high, do travel-dynamic influences have a noticeable effect on the measured level H.

For the purpose of determining the viscosity of the oil, after the internal combustion engine has started in the cold state the engine oil level H is measured and evaluated with the oil level sensor during a defined time window on the curve. The gradient –dH/dt is proportional to the viscosity of the oil.

To obtain more precise information on the viscosity, the oil temperature is determined at the time of starting the internal combustion engine and the value for viscosity derived from the change in measured level H after a period of time is corrected to allow for the influence of temperature T.

Another improvement to the measured value is obtained when, in addition to the temperature T of the oil, the rotational speed of the internal combustion engine is allowed for in determining the viscosity. The "absorbed volume" of an engine, that is the change in level in the reservoir, increases as the engine speed increases.

The difference in level in the reservoir and the level in the measuring chamber influences the rate of change of the measured level H. In an advantageous design of the method, the value for viscosity determined from the change in measured level H after a period of time is corrected to allow not only for the influence of temperature but also for the influence of engine speed. For this purpose, the variation in speed is also measured over the time window of viscosity measurement.

When the engine runs faster it also heats up faster, i.e. the gradient dT/dt becomes greater. Therefore, if the speed curve is not known, it is possible to draw approximate conclusions concerning the influence of engine speed on the change in oil level from the change in oil temperature after a period of time. The quantity –dH/dT is also a measure of the viscosity of the oil.

The value for viscosity derived by the method described above is collected in a central control unit and further processed, for example for diagnostic purposes. Thus, for instance, the viscosity of the engine oil can be traced over lengthy periods of time and a warning signal can be output when a critical value is reached.

What we claim is:

1. Method for determining the viscosity of an operating liquid of an internal combustion engine by establishing the level of the operating liquid, wherein
   a sensor is provided for establishing the level of the operating liquid, said sensor having a measuring chamber that is connected via a damping device to a reservoir of the operating liquid,
   on starting the internal combustion engine the variation in the level (H) of the operating liquid in the measuring chamber of the sensor is measured, and
   the variation in level (H) against time is used as a measure of viscosity.

2. Method in accordance with claim 1, wherein the temperature (T) of the operating liquid is measured during the starting operation and allowed for in the determination of the viscosity.

3. Method in accordance with claim 2, wherein the speed of the internal combustion engine is measured after the starting operation and allowed for in the determination of the viscosity.

4. Method in accordance with claim 1, wherein the temperature of the operating liquid during the starting operation and the variation in the temperature of the operating liquid are allowed for in the determination of the viscosity.

5. A method of determining the viscosity of an operating liquid in an internal combustion engine having a liquid reservoir containing some of said operating liquid, using a sensor having a measuring chamber containing some of said operating liquid, comprising the following steps:
   a) starting and running said engine;
   b) communicating and allowing said operating liquid to flow between said measuring chamber of said sensor and said liquid reservoir;
   c) during said step a) and said step b), measuring a liquid level of said operating liquid and a variation of said liquid level in said measuring chamber of said sensor; and
   d) determining said viscosity of said operating liquid from said variation of said liquid level in said measuring chamber over time.

6. The method according to claim 5, wherein said step b) further comprises damping said flow of said operating liquid between said measuring chamber and said liquid reservoir so that said variation of said liquid level in said measuring chamber dampedly follows and lags behind a variation of a level of said operating liquid in said liquid reservoir with a time delay.

7. The method according to claim 5, wherein said operating liquid is an engine lubricating oil of said internal combustion engine, and said liquid reservoir is an oil sump of said internal combustion engine.

8. The method according to claim 5, wherein said step c) comprises determining said variation of said liquid level in said measuring chamber over time during a time interval directly following said starting of said engine while said liquid level is monotonously reducing, and said step d) comprises determining said viscosity from said variation during said time interval.

9. The method according to claim 8, wherein said step d) comprises determining said viscosity as a value proportional to –dH/dt, where H represents said liquid level and t represents said time during said time interval.

10. The method according to claim 5, further comprising measuring a temperature of said operating liquid during said step a), and wherein said step d) further comprises taking said temperature into account in said determining of said viscosity.

11. The method according to claim 10, further comprising determining a variation of said temperature over time following said starting of said engine, and wherein said step d) further comprises taking said variation of said temperature into account in said determining of said viscosity.

12. The method according to claim 10, wherein said step d) comprises determining said viscosity as a value proportional to –dH/dT, where H represents said liquid level and T represents said temperature.

13. The method according to claim 10, further comprising measuring an operating speed of said internal combustion engine during said step a), and wherein said step d) further comprises taking said operating speed into account in said determining of said viscosity.

14. The method according to claim 5, further comprising measuring an operating speed of said internal combustion engine during said step a), and wherein said step d) further comprises taking said operating speed into account in said determining of said viscosity.

15. The method according to claim 14, further comprising determining a variation of said operating speed over time following said starting of said engine, and wherein said step d) further comprises taking said variation of said operating speed into account in said determining of said viscosity.

16. The method according to claim 5, further comprising comparing said viscosity to a critical value and outputting a warning signal if said viscosity reaches or passes said critical value.

* * * * *